US00PP31226P2

(12) United States Plant Patent
Grover et al.

(10) Patent No.: US PP31,226 P2
(45) Date of Patent: Dec. 10, 2019

(54) ***PULMONARIA* PLANT NAMED 'LISA MARIE'**

(50) Latin Name: ***Pulmonaria* spp.**
Varietal Denomination: LISA MARIE

(71) Applicants: Lisa Grover, Belvidere, IL (US); Bradley Grover, Belvidere, IL (US)

(72) Inventors: Lisa Grover, Belvidere, IL (US); Bradley Grover, Belvidere, IL (US)

( * ) Notice: Subject to any disclaimer, the term of this patent is extended or adjusted under 35 U.S.C. 154(b) by 0 days.

(21) Appl. No.: 15/998,203

(22) Filed: Jul. 12, 2018

(51) Int. Cl.
*A01H 5/02* (2018.01)
*A01H 6/00* (2018.01)

(52) U.S. Cl.
USPC ..... Plt./473

(58) Field of Classification Search
USPC ..... Plt./473
See application file for complete search history.

*Primary Examiner* — Susan McCormick Ewoldt
(74) *Attorney, Agent, or Firm* — Cassandra Bright

(57) ABSTRACT

A new and distinct *Pulmonaria* cultivar named 'LISA MARIE' is disclosed, characterized by large, long leaves, and large, pink-red flowers. The new variety is a *Pulmonaria*, normally produced as an outdoor garden or container plant.

3 Drawing Sheets

Latin name of the genus and species: *Pulmonaria* spp.
Variety denomination: 'LISA MARIE'.

BACKGROUND OF THE INVENTION

The new *Pulmonaria* cultivar is a product of a natural occurring mutation, discovered by the inventors, Lisa and Bradley Grover, in Belvidere, Ill. This new variety was found and selected in June 1995 in a private garden.

The parent variety is an unpatented, unnamed variety of *Pulmonaria*. The new variety was discovered as a naturally occurring whole plant mutation.

Asexual reproduction of the new cultivar 'LISA MARIE' by vegetative cuttings was first performed during 2014, at a nursery in Belvidere, Ill. Subsequent propagation has shown that the unique features of this cultivar are stable and reproduced true to type in multiple successive generations.

SUMMARY OF THE INVENTION

The cultivar 'LISA MARIE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LISA MARIE' These characteristics in combination distinguish 'LISA MARIE' as a new and distinct *Pulmonaria* cultivar:

1. Distinctively larger, longer leaves.
2. Uniquely large flowers.
3. Unusually pink-red flower color.

PARENT COMPARISON

Plants of the new cultivar 'LISA MARIE' are similar to plants of the parent variety in most horticultural characteristics, however, plants of the new cultivar 'LISA MARIE' differ in the following;

1. The new variety has larger, longer leaves.
2. The new variety has larger flowers.
3. The new variety has a brighter pink flower color.

COMMERCIAL COMPARISON

Plants of the new cultivar 'LISA MARIE' can be compared to the commercial variety *Pulmonaria* 'Raspberry Splash', U.S. Plant Pat. No. 12,138. These varieties are similar in most horticultural characteristics; however 'LISA MARIE' differs in the following:

1. The new variety has larger, longer leaves.
2. The new variety has larger flowers.
3. The new variety has a brighter flower color.

Plants of the new cultivar 'LISA MARIE' can be compared to the unpatented commercial variety *Pulmonaria* 'Trevi Fountain'. These varieties are similar in most horticultural characteristics; however 'LISA MARIE' differs in the following:

1. 'Lisa Marie' has larger, longer leaves.
2. 'Lisa Marie' has larger flowers.
3. 'Lisa Marie' has pink-red flower, flowers of 'Trevi Fountain' are blue.

BRIEF DESCRIPTION OF THE PHOTOGRAPHS

The accompanying photograph in FIG. 1 illustrates in full color a typical plant non-flowering plant of 'LISA MARIE' grown in the ground outdoors in Ohio. Age of the plant photographed in FIG. 1 is approximately 5 years.

Figure 1:
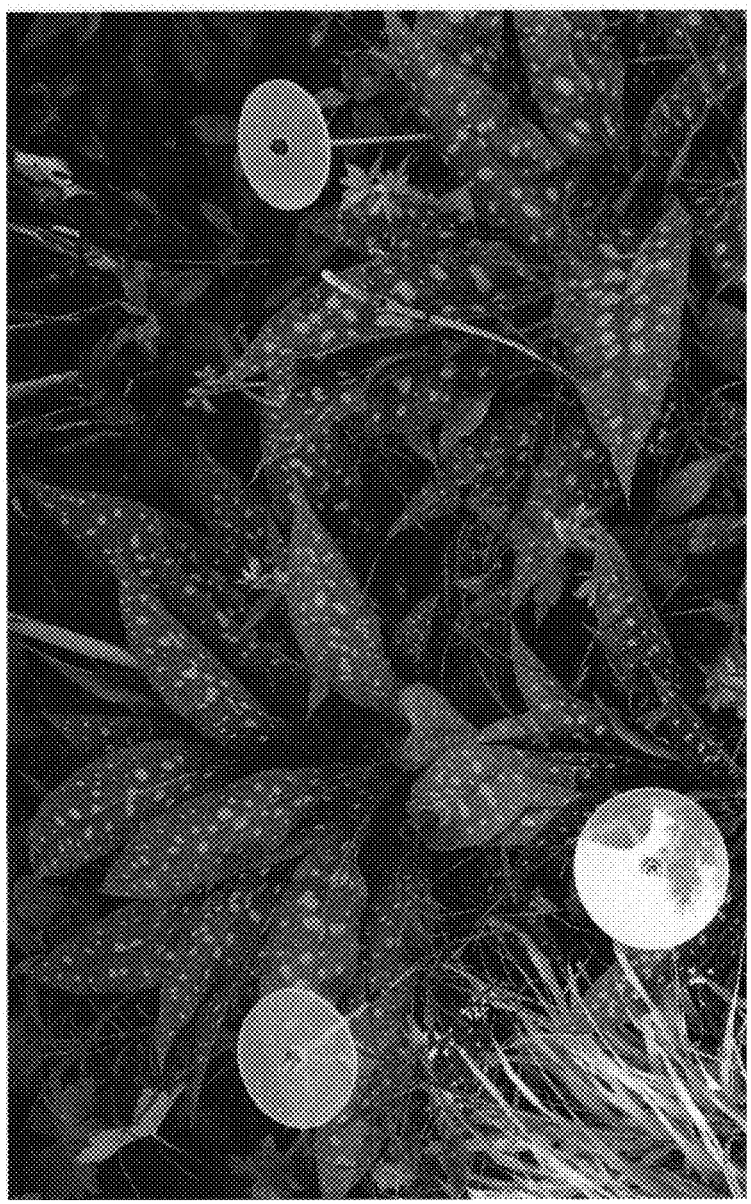
Figure 2:
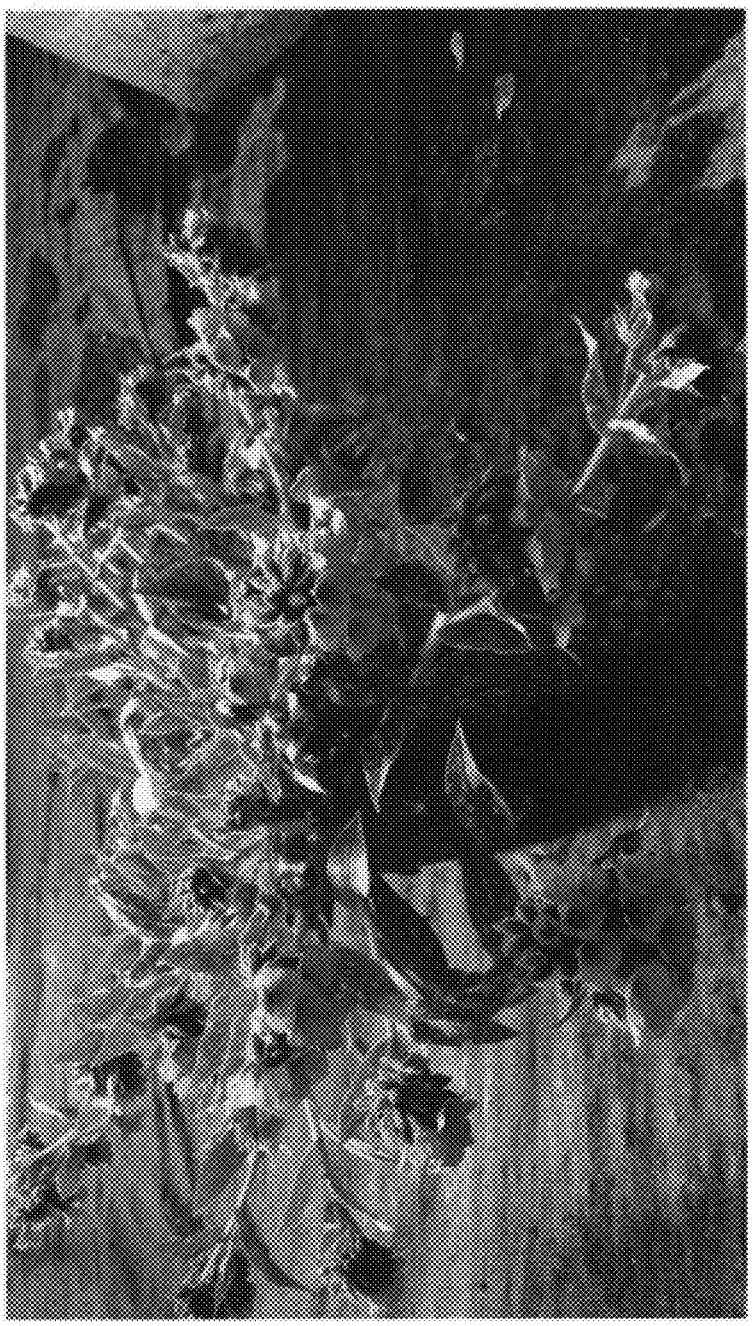
FIG. 2 illustrates in full color a flowering plant grown in a 1 gallon pot. Age of the plant photographed in FIG. 2 is approximately 1 year.
Figure 3:
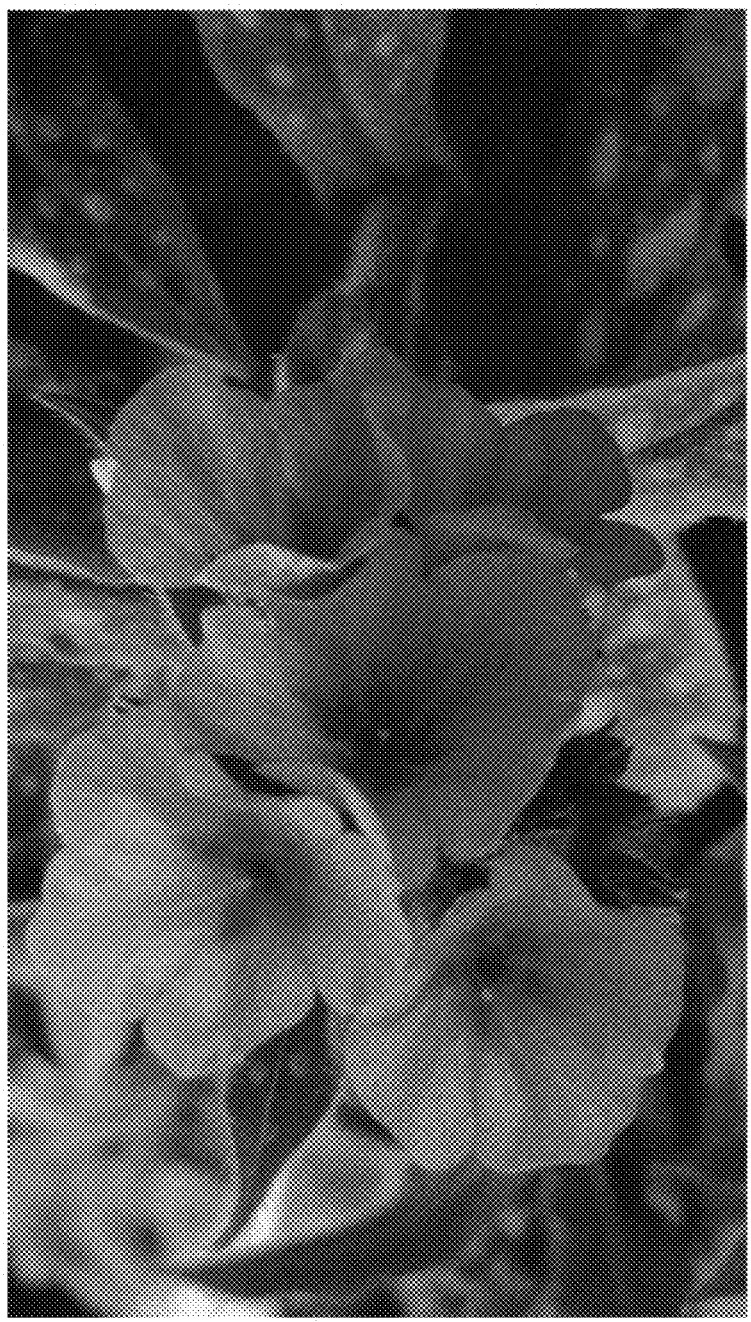
FIG. 3 illustrates a close up of a single flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'LISA MARIE' plants grown in a nursery in Belvidere, Ill., under natural lighting. The plants were about 1 year old in 1 gallon containers. The growing temperature ranged from 12° C. to 27° C. Measurements and numerical values represent averages of typical plant types.

Botanical classification: *Pulmonaria* spp. 'LISA MARIE'.

PROPAGATION

Time to rooting: 4-6 weeks at approximately 13° C.

Root description: Fibrous, brown, not accurately measured with R.H.S. chart.

PLANT

Plant shape: Horizontal oval, and mounding.

Plant spread: Approximately 107 cm.

Plant height:

*Top of flowering plane.*—30 cm.

*Top of foliar plane.*—48 cm.

Growth rate: Moderate to rapid.

Length of primary stem: Approximately 18 cm.

Diameter of primary stem: Approximately 0.5 cm.

Stem:

*Color.*—Yellow-Green 147C with Greyed-Orange 176 hairs.

*Texture.*—Pubescent.

Lateral branches: None, basal branches.

FOLIAGE

Leaf:

*Arrangement.*—Radial.

*Quantity.*—Approximately 40.

*Average length.*—Approximately 18 to 30 cm.

*Average width.*—Approximately 10 cm.

*Shape of blade.*—Lanceolate.

*Apex.*—Acute.

*Base.*—Cuneate.

*Attachment.*—Sessile

*Margin.*—Entire.

*Texture of top surface.*—Pubescent.

*Texture of bottom surface.*—Pubescent.

Color:

*Young foliage upper side.*—Near RHS Green N137A with Green 138D spots.

*Young foliage under side.*—Near RHS Yellow-Green 147C.

*Mature foliage upper side.*—Near RHS Green N137A with Green 138D spots.

*Mature foliage under side.*—Near RHS Yellow-Green 147B.

Venation:

*Type.*—Pinnate.

*Venation color upper side.*—Near RHS Yellow-Green 144D.

*Venation color under side.*—Near RHS Yellow-Green 144D.

Petiole:

*Average length.*—Approximately 9 cm.

*Diameter.*—Approximately 0.5 cm.

*Color.*—Near RHS Yellow-Green 144B.

*Texture.*—Pubescent.

FLOWER

Natural flowering season: Spring.

Inflorescence type and habit: Cyme composed of campanulate flowers.

Quantity of flowers: About 130 buds and 30 fully opened flowers per plant, at one time.

Inflorescence size:

*Diameter.*—Approximately 7 cm.

*Height.*—Approximately 4 cm.

Individual flowers:

*Diameter.*—1.5 cm.

*Length.*—2 cm.

*Flower tube length.*—1 cm.

*Flower tube diameter at distal end* (*throat opening*).—0.3 cm.

*Flower tube diameter at proximal* (*base*) *end.*—0.2 cm.

*Lastingness.*—About 10 to 15 days, depending upon environmental conditions.

Petals:

*Arrangement.*—Fused, with upper edges separated.

*Quantity.*—5.

*Shape.*—Funnel-shaped.

*Length from throat.*—1.3 cm.

*Width.*—1 cm.

*Apex.*—Rounded.

*Texture.*—Smooth.

*Margin.*—Entire.

*Petaloids present.*—No.

*Color.*—When opening: Inner surface: RHS Red 53C. Base Greyed-Purple 185C. Outer surface: RHS Red-Purple 64C, base Greyed-Purple 184A. Fully opened: Inner surface: RHS Red-Purple 58D, flush near mid-vein 61C, base Greyed-Purple 185C. Outer surface: RHS Red-Purple 58D, base Greyed-Purple 184A. Flower throat (inside): RHS Greyed-Purple 184C. Flower throat, vein: RHS Greyed-Purple 184A. Flower tube (outside): RHS Greyed-Purple 183C. Flower tube, vein: RHS Greyed-Purple 182A. Petals fading to: RHS Red 55A, flushed Greyed-Red 182A.

Bud:

*Shape.*—Tubular.

*Length.*—1.6 cm.

*Diameter.*—1 cm.

*Color.*—Near RHS Greyed-Purple 187B.

Peduncle:

*Length.*—0.5 cm.

*Diameter.*—0.1 cm

*Color.*—Near RHS Yellow-Green 148A.

*Texture.*—Pubescent.

*Orientation/aspect.*—Straight.

*Strength.*—Good.

Pedicel:

*Length.*—0.3 cm.

*Diameter.*—0.15 cm.

*Color.*—Near RHS White NN155.

*Orientation/aspect.*—Straight.

*Strength.*—Good.

Calyx:

*Shape.*—Tubular.

*Size.*—1.5 cm.

Sepals:
*Shape*.—Lanceolate.
*Quantity per flower*.—
*Length*.—Approximately 1 cm.
*Width*.—Approximately 0.5 cm.
*Apex*.—Acute.
*Margin*.—Entire.
*Texture*.—Pubescent.
*Color*.—Outer surface: Near RHS Yellow-Green 147B with Greyed-Purple 186C striation. Inner surface: Near RHS Yellow-Green 147B.

REPRODUCTIVE ORGANS

Stamens:
*Number*.—5.
*Filament length*.—Approximately 1 cm.
Anthers:
*Shape*.—Linear.
*Length*.—Approximately 0.3 cm.
*Color*.—Near RHS Greyed-Purple N186A.

Pistil:
*Number*.—1.
*Length*.—Approximately 1.2 cm.
*Style*.—Length: Approximately 1 cm. Color: Near RHS White NN155B.
Stigma:
*Shape*.—Round.
*Color*.—Near RHS Yellow 4D.
*Ovary color*.—Near RHS White 155B with a Greyed-Purple 185C tip.

OTHER CHARACTERISTICS

Seeds and fruits: None observed.
Disease/pest resistance: None observed.
Temperature tolerance range: USDA zones 3-8.

What is claimed is:

1. A new and distinct cultivar of *Pulmonaria* plant named 'LISA MARIE' as herein illustrated and described.

* * * * *